United States Patent [19]
Su

[11] Patent Number: 5,804,684
[45] Date of Patent: Sep. 8, 1998

[54] METHOD FOR ISOLATING NUCLEIC ACIDS

[75] Inventor: Xing Su, Belmont, Mass.

[73] Assignee: The Theobald Smith Research Institute, Inc., Boston, Mass.

[21] Appl. No.: 519,039

[22] Filed: Aug. 24, 1995

[51] Int. Cl.⁶ ................................................ C07H 21/00
[52] U.S. Cl. .................. 536/25.4; 536/25.41; 536/25.42; 435/270; 422/70; 422/101
[58] Field of Search ...................... 422/70, 101; 435/270; 536/25.4, 25.41, 25.42

[56] References Cited

U.S. PATENT DOCUMENTS

| | | | |
|---|---|---|---|
| 4,160,803 | 7/1979 | Potts | 422/101 |
| 4,902,481 | 2/1990 | Clark et al. | 422/101 |
| 4,923,978 | 5/1990 | McCormick | 536/25.4 |
| 5,063,162 | 11/1991 | Kiefer | 435/270 |
| 5,108,704 | 4/1992 | Bowers et al. | 422/70 |
| 5,187,083 | 2/1993 | Mullis | 435/91 |
| 5,205,989 | 4/1993 | Aysta | 422/101 |
| 5,217,593 | 6/1993 | MacConnell | 204/299 R |
| 5,219,528 | 6/1993 | Clark | 422/101 |
| 5,234,809 | 8/1993 | Boom et al. | 435/91.2 |
| 5,234,824 | 8/1993 | Mullis | 435/91 |
| 5,264,184 | 11/1993 | Aysta et al. | 422/101 |
| 5,346,994 | 9/1994 | Chomczynski | 530/419 |
| 5,417,923 | 5/1995 | Bojanic et al. | 422/101 |

FOREIGN PATENT DOCUMENTS

| | | |
|---|---|---|
| 0240191 | 10/1987 | European Pat. Off. . |
| 0512767 | 11/1992 | European Pat. Off. . |
| 0512768 | 11/1992 | European Pat. Off. . |
| 9112079 | 8/1991 | WIPO . |

OTHER PUBLICATIONS

Freifelder, *Physical Biochemistry, Second Edition,* W. H. Freeman & Co., New York, NY, 1982, only copies of pp. 257–262 supplied by applicant.

Burtis et al., *Tietz Textbook of Clinical Chemistry, Second Edition,* W. B. Saunders Company, New York, NY, 1994, only copies of pp. 210–211 supplied by applicant.

Schleif & Wensink, *Practical Methods in Molecular Biology,* Springer–Verlag, New York, NY, 1981, only pp. 93–111 supplied.

"Proteinase K for Nucleic Acid Research," *BMBiochemica,* 1(5), 3 (Dec. 1984).

Beil et al., "Isolation of DNA from Fungal Mycelia and Sclerotia without Use of Density Gradient Ultracentrifugation," *Analytical Biochem.,* 154, 21–25 (1986).

Beji et al., "A Rapid Chemical Procedure for Isolation and Purification of Chromosomal DNA from Gram–Negative Bacilli," *Analytical Biochem.,* 162, 18–23 (1987).

*Primary Examiner*—John Kight
*Assistant Examiner*—L. Eric Crane
*Attorney, Agent, or Firm*—Banner & Witcoff, Ltd.

[57] ABSTRACT

The invention features a method of isolating nucleic acid in a substantially purified form, including the steps of: a) contacting a biological sample which contains aggregated nucleic acid with a matrix comprising a solid hydrophilic organic polymer without an effective positive charge under conditions which permit the nucleic acid to bind to the matrix; and b) recovering nucleic acid from the matrix.

20 Claims, 1 Drawing Sheet

METHOD FOR ISOLATING NUCLEIC ACIDS

The invention was made using U.S. Government Funds, and therefore the U.S. Government has certain rights in the invention.

FIELD OF THE INVENTION

The invention relates to nucleic acid isolation, and more particularly to compositions and methods useful for isolation of nucleic acids.

BACKGROUND OF THE INVENTION

Nucleic acid purification from biological sources or post-enzymatic reactions is frequently a primary step in molecular biology studies and diagnostic tests. Many techniques have been developed to isolate DNA and RNA, for example, phenol extraction, alcohol precipitation, density gradients, dialysis, ion exchange, electroelution, silica binding, membrane filtration, and column filtration.

U.S. Pat. No. 5,346,994 to Chomczynski discloses a liquid nucleic acid isolation method employing a reagent mixture of phenol, chaotropic salts and stabilizers. The procedure involves cell lysis and separation of DNA, RNA and proteins in different phases by centrifugation.

U.S. Pat. Nos. 5,187,083 and 5,234,824 to Mullis disclose DNA isolation methods which rely on physical trapping of high molecular weight DNA on membranes, such as cellulose acetate filters. These methods are designed for large DNA and are not effective for generally isolating DNAs of any size or molecular weight.

A common approach to isolating and purifying nucleic acids involves binding of the negatively charged phosphodiester backbone of the nucleic acid to a positively charged polymer by electrostatic interactions (ion exchange). U.S. Pat. No. 4,935,342 to Seligson et al. discloses a nucleic acid isolation method in which positively charged anion exchange materials are utilized. The nucleic acids are released from the matrices in solutions of high ionic strength (i.e., high salt concentration). However, removal of the salt is often necessary before the nucleic acids may be utilized further.

U.S. Pat. No. 5,329,000 to Woodard et al. discloses a method of isolating DNA using a silicon tetrahydrazide matrix. Similarly, U.S. Pat. No. 5,342,931 to Woodard et al., discloses a DNA isolation method using a matrix of hydrated silica. In both cases, DNA binds to the inorganic matrix and is released in heated water.

U.S. Pat. No. 4,923,978 discloses a method of isolating nucleic acids using hydroxylated matrices in a column. In this approach, proteins are subtracted from the biological sample via adsorption onto the matrix, and nucleic acids flow through the matrix. However, because this procedure is subtractive, further purification and concentration of the nucleic acid is often required.

One object of the invention is to isolate nucleic acid from a biological sample in a simple, fast, and efficient process. Another object is to provide a method which avoids high speed centrifugation and phase separation to isolate a nucleic acid. Another object is to provide for highly quantitative recovery of nucleic acid regardless of its molecular weight. Another object of the invention is to isolate nucleic acid from a number of samples simultaneously, thus saving time and effort and providing for subsequent simultaneous processing of the samples. Yet another object of the invention is to provide for simultaneous processing and recovery of even small amounts of nucleic acids from multiple samples. Another object of the invention is to avoid the risk of loss of an isolated nucleic acid by providing a nucleic acid preparation which does not require further concentration from a large volume or does not require further purification. Yet another object of the invention is to provide for high yield recovery of nucleic acid within a broad size range. Another object is to provide a method of nucleic acid isolation that is environmentally friendly, i.e., that avoids the use of toxic chemicals, corrosive agents or chaotropic salts.

SUMMARY OF THE INVENTION

The invention is based on a method and apparatus for nucleic acid isolation. The invention utilizes the properties of aggregated nucleic acids to isolate and purify nucleic acids from contaminants such as other cellular components. The invention is based on the discovery that aggregated nucleic acid is capable of binding reversibly to a solid, hydrophilic organic matrix without an effective positive charge.

The invention therefore encompasses a method of isolating nucleic acid in a substantially purified form, the method comprising the steps of: a) contacting a biological sample comprising aggregated nucleic acid with a matrix under conditions which permit nucleic acid in the sample to reversibly bind to the matrix, the matrix comprising a solid hydrophilic organic polymer without an effective positive charge; and b) recovering nucleic acid from the matrix.

Preferably, in the recovering step, the nucleic acid is eluted from the matrix in substantially purified and concentrated form. The recovery step may also comprise dissociation and/or solubilization of the nucleic acid aggregates in water or a low salt buffer.

As used herein, "biological sample" refers to a sample of biological or biochemical origin; "substantially purified" refers to recovery of nucleic acid which is at least 80% and preferably 90–95% purified with respect to removal of a contaminant, e.g., cellular components such as protein, lipid or salt; thus, the term "substantially purified" generally refers to separation of a majority of cellular proteins or reaction contaminants from the sample, so that compounds capable of interfering with the subsequent use of the isolated nucleic acid are removed; "bind to" refers to reversible binding via weak forces such as Van der Waals interactions, and does not refer to electrostatic interactions, affinity binding or physical trapping. As used herein, "Van der Waals interactions" refer to the weak forces between atoms and molecules due to induced or instantaneous dipole movements, which may allow packing together of organic compounds such as nucleic acid and other hydrophilic organic materials (matrix). "Electrostatic interactions" refer to positive (+) and negative (−) charge attractions; "affinity binding" refers to the sequence- or conformation-specific and directional binding between a molecule and its complementary molecule; and "physical trapping" refers to retaining of nucleic acid based on the relatively large size of the nucleic acid and small size of holes in the matrix.

As used herein, "without an effective positive charge" refers to a matrix having a net (i.e., overall) neutral or a net negative charge, or a matrix which does not possess sufficient positive charge to attract, bind or retain a measurable or detectable amount of nucleic acid in low ionic strength buffer (i.e., <10 mM of Na+, pH 5–10). A net charge is calculated by adding together the positive and negative charges in the repeating units of the polymer that constitute the matrix. Thus, a matrix without an effective positive charge is not suitable for use as an ion exchange material for nucleic acid purification by conventional methods.

The terms "aggregate" and "aggregation" refer to the tendency of large macromolecules, such as nucleic acids, to combine into clusters or clumps. Thus, nucleic acids are considered "aggregated" when they precipitate or separate from the dissolved state. A nucleic acid is considered aggregated for the purposes of the invention when essentially no nucleic acid (i.e., less than 90% and preferably less than 98% of the nucleic acid present prior to aggregation) remains in solution upon collection of the precipitated nucleic acid by centrifugation, e.g., 5,000 to 10,000 rpm for approximately 10 min.

The term "hydrophilic organic polymer" refers to a polymer made of repeating units of organic compounds, i.e., natural and synthetic forms thereof. The polymer is insoluble in water and alcohol (at <50 degrees C.) and has sufficient amounts of polar groups accessible to water molecules such that water can be retained and absorbed by the matrix. Preferably, the matrix comprises a polymer in which substantially all of the repeat units include polar, uncharged groups at neutral pH. Polar groups are those which have abilities to form hydrogen bonds with water molecules.

Preferably, the matrix is a hydrophilic naturally occurring compound or a synthetic organic compound or a hydrophilic derivative of a hydrophobic compound. Hydrophilic derivatives of a hydrophobic compound (backbone), such as a plastic material, can be obtained by modifying the backbone with the addition of polar groups, including hydroxyl groups (OH), carboxyl groups (COOH), amino groups ($NH_2$), groups which are neutral at pH >7, and thiol groups (SH), such that the surfaces of fibrous and particulate matrices comprising this polymer then possess hydrophilic properties.

A hydrophilic compound or a modifiable hydrophobic backbone is selected from the group of polysaccharides including cellulose, rayon, cellulose acetate, cellulose triacetate, chitin and agarose. It can also be selected from the group of protein/polypeptides including leather, silk and wool. It can also be selected from synthetic gels including polyacrylamide, hydrogel (i.e., copolymer of poly(vinyl alcohol) and collagen). It may also be selected from the group of synthetic fibers including polyamides (nylon), polyesters, polyacrylonitrile (acrylic), polyurethane (spandex). It can also be selected from the group of synthetic plastics including polycarbonate, phenol-formaldehyde resins, polysulfide, poly(vinyl butyryl), poly(vinyl chloride), poly(vinylidene chloride), poly(ethylene), and polystyrene.

Fibrous or particulate forms of a polymer can be readily prepared by mechanical means well-known in the art.

In preferred embodiments, the method further includes an initial step of contacting the biological sample with a proteolytic enzyme under conditions sufficient to subject the sample to proteolysis and preferably release of the nucleic acid.

The method further includes the step of aggregating the nucleic acid, wherein the nucleic acid is aggregated by contacting the biological sample with a precipitant selected from the group consisting of organic solvents, soluble organic polymers and salts, wherein the organic solvent may be any one of isopropanol, ethanol, acetone, and organic polymers including but not limited to polyethylene glycol (PEG), and wherein the salt may include but is not limited to NaCl and LiCl. Co-precipitants, such as glycogen, also may be used to facilitate the precipitation of nucleic acid present in only small quantities; for example, in the form of heteroaggregates. The presence of a co-precipitant is not required according to the invention, but serves to increase the efficiency of aggregate formation.

Small molecules and digested proteins do not bind to the matrices and thus may be separated from the nucleic acid by washing the adsorbed, aggregated nucleic acid. Therefore, the method may also include a washing step using solutions that contain a precipitant at a concentration sufficient to maintain a nucleic acid in aggregated form.

The invention also includes an apparatus for isolating nucleic acid in a substantially purified form from multiple biological samples simultaneously, the apparatus comprising: plural housings for isolation of nucleic acid from plural biological samples, wherein each housing comprises an inlet and an outlet and defines a flowpath for flow of a biological sample therethrough, the flowpath comprising a matrix comprising a solid hydrophilic organic polymer without a net positive charge, and support means for holding plural housings in place such that nucleic acid in plural biological samples may be handled and isolated simultaneously.

Preferably, each housing of the apparatus further includes a barrier means to allow flow of liquid along the flowpath and through the housing outlet, but to prevent the matrix from exiting the housing via the outlet. Most preferably, the housing comprises a lower portion leading to the outlet and the barrier is positioned within the lower portion of the housing. The apparatus may also include means for connecting the plural housings to a vacuum or pressure source. The barrier may be any material which prevents the matrix from exiting the housing but which allows liquid comprising nucleic acid to flow through and exit the housing, for example, a mesh screen, cotton fibers, synthetic fibers, tissue paper, or siliconized glass fibers. The apparatus may also include a collection tray for simultaneously collecting waste or plural nucleic acid samples. In a preferred embodiment, the apparatus may be subjected to vacuum force, pressure force or low centrifugation force. In another embodiment, the apparatus is constructed such that it does not allow for cross-contamination of the samples.

The method and apparatus of the present invention permits the isolation of nucleic acid having essentially any molecular weight or form (i.e., circular, linear, etc.) in a rapid and high-yield manner. The apparatus allows for such isolation from plural samples simultaneously.

The nucleic acid isolated as described herein may be of any molecular weight and in single-stranded or double-stranded form; i.e., small oligonucleotides such as 10–50 bases in length, small nucleic acid fragments of, for example, 100 bases–500 bases in length, or relatively longer fragments of 1000 bases–10,000 bases in length. Alternatively, high molecular weight nucleic acid, e.g., 50 kb–500 kb may be isolated as described herein. Preferably, a nucleic acid isolated according to the invention will be in the range of 100 bases to 100 kilobases.

The nucleic acid sample applied to the matrix according to the methods described above may be in any convenient volume. Where large-scale isolation is contemplated, the applied volume may be correspondingly large, e.g., 1 liter, 500 ml, 100 ml, 50 ml, etc. Alternatively, where other than large-scale isolation is contemplated, a correspondingly smaller volume may be applied to the matrix, e.g., less than 50 ml, more preferably, less than 5 ml, less than 500 µl; e.g., 1–100 µl.

The volume of nucleic acid isolated according to the invention may be in any selected volume which is sufficient to saturate the matrix. For example, for nucleic acid isolation on a large-scale, the volume of isolated nucleic acid may be correspondingly large, e.g., 1–100 ml, as described above for the applied volume. Alternatively, the isolated nucleic acid may be recovered in a smaller volume, e.g., less than 500 µl, 250 µl, 100 µl; e.g., 1–50 µl.

The nucleic acid applied to the matrix, as described herein, may be any amount, that amount being determined by the amount of matrix. Preferably, the amount of nucleic acid (and plus co-precipitant, if desired) applied to the matrix is less than the dried weight of the matrix, typically in the range of 1/10,000 to 1/10 (weight nucleic acid/ matrix). The amount of nucleic acid applied to the matrix may be as much as 100 gm or as little as 1 pg. Preferably, the amount of nucleic acid applied to the matrix is less than a total of 100 mg, more preferably in the range of 10 mg–0.1 ng, and most preferably, in the range of 500 µg–1 ng. The nucleic acid isolated from the matrix will generally be in an amount which is about 90% or more than the amount of nucleic acid applied to the matrix.

The invention is particularly useful in procedures wherein large numbers of samples are handled simultaneously, for example, in newborn screening, where as many as 4–5 million samples of newborn blood nationwide are analyzed annually. Molecular screening of newborns is still in its infancy and large scale screening is still difficult, mainly due to lack of a suitable nucleic acid purification method.

The invention provides for easy simultaneous recovery of plural nucleic acid samples. In addition, because the inventive methods and devices do not allow for leaking between sample chambers, the danger of cross-contamination of samples is significantly reduced throughout the isolation procedure, i.e., before, during and after isolation of the sample from the sample matrix. These advantages are especially important for uses contemplated in the invention, i.e., where hundreds of individual samples, e.g., 100, 200–500, or thousands, e.g., 1000, 2000, 3000, 4000–6000, or even up to ten thousand or one-hundred thousand individual samples are analyzed simultaneously.

The invention thus provides for high yield recovery of relatively pure nucleic acid molecules from a biological sample. The nucleic acid may be recovered efficiently from a number of samples simultaneously, thus saving time and effort and providing for subsequent simultaneous processing or analysis of numerous nucleic acid samples, if desired. Any number of samples may be subjected to isolation simultaneously according to the invention, e.g., a single sample, two samples, tens of samples, 100's and even thousands of samples are conveniently isolated using the devices and methods disclosed herein. The invention thus provides for isolation of nucleic acids from hundreds or thousands of samples routinely in an efficient and safe manner. The number of simultaneously isolated samples is only limited by the number of sample chambers which are present in a single format. A format may include a single planar surface containing numerous individual sample chambers or it may include multiple surfaces; the latter format would include multiple stacked surfaces or multiple side-by-side surfaces.

Nucleic acids may be selectively recovered from impure samples such as body fluids, cells, tissues or other types of biological samples according to the invention. Exceedingly small amounts of nucleic acid molecules may be simultaneously and quantitatively recovered according to the invention. For example, 80–90% of the small amount of DNA or RNA present in the dried blood spot samples that are routinely assayed in newborn screening (e.g., equivalent to 15 µl newborn blood or about 0.4 µg DNA) can be recovered. The yield of recovery is mainly dependent on the quality of the dried blood sample rather than the procedure itself. Because the invention provides a nucleic acid preparation that does not require concentration from a large volume, the invention avoids risk of loss of the isolated nucleic acid.

Nucleic acids isolated according to the invention, will be useful, for example, in assays for detection of the presence of a particular nucleic acid in a sample. Such assays are important in the prediction and diagnosis of disease, forensic medicine, epidemiology and public health. For example, isolated DNA may be subjected to hybridization and/or amplification to detect the presence of an infectious virus or a mutant gene in an individual, allowing determination of the probability that the individual will suffer from a disease of infectious or genetic origin. The ability to detect an infectious virus or a mutation in one sample among the hundreds or thousands of samples being screened takes on substantial importance in the early diagnosis or epidemiology of an at-risk population for disease, e.g., the early detection of HIV infection, cancer or susceptibility to cancer, or in the screening of newborns for diseases, where early detection may be instrumental in diagnosis and treatment.

In addition, the method can also be used in basic research labs to isolate nucleic acid from cultured cells or biochemical reactions. The purified nucleic acid can be used for enzymatic modification such as restriction enzyme digestion, sequencing and amplification.

Further objects and advantages of the invention will be apparent in light of the following description and the claims.

BRIEF DESCRIPTION OF THE FIGURES

Before describing the invention in detail, the drawings will be briefly described.

DETAILED DESCRIPTION OF THE INVENTION

The invention encompasses a method and apparatus for nucleic acid isolation and concentration, and takes advantage of the discovery that aggregated nucleic acid binds reversibly to a solid, hydrophilic organic matrix without an effective positive charge.

The invention utilizes the properties of aggregated nucleic acid to isolate and separate nucleic acid from other cellular components. Nucleic acid can be released in aqueous buffer from cells or tissues by essentially any known method, such as mechanical disruption, sonication, detergent solubilization, and the like. Once released from cells or tissues and separated from insoluble materials, nucleic acid in solution is allowed to form aggregates in the presence of precipitants.

According to the invention, a nucleic acid aggregate is contacted with a solid, hydrophilic organic matrix without an effective positive charge under conditions and for a time sufficient to allow it to bind reversibly to the matrix. If desired, the matrix-nucleic acid complex may be washed to remove contaminants, then dissociated and/or solubilized, and nucleic acid recovered in water or low salt buffer. The method of the present invention permits the investigator or technician to isolate nucleic acid of essentially any molecular weight in a rapid, high-yield manner.

The nucleic acid aggregate binds to the matrix in suspension or on a column; digested proteins and salts do not bind and thus are separated from nucleic acid in that they flow through the matrix. The bound nucleic acid is eluted from the matrices and recovered in a substantially pure and concentrated state, suitable for direct use.

Solid hydrophilic organic polymers that constitute a matrix useful according to the invention fall within the definition provided hereinabove. A matrix according to the invention will include any solid, hydrophilic organic matrix without an effective positive charge that reversibly binds nucleic acid through Van der Waals interactions and not by electrostatic interactions, affinity binding, or physical trapping. Preferably, the matrix is essentially neutral, i.e., without any positive or negative charge.

The term "solid matrix", as used herein, encompasses a polymer that is substantially insoluble in water and alcohol at less than about 50 degrees centigrade. Preferably, a solid matrix is in particulate form, with the particles being in the micro-meter range (preferably, 5–500 $\mu$meters) or the millimeter range (preferably, 0.1–10 mmeters); or is in fibrous form with the fibers being micro-meter in diameter and of any desired length.

The term "polymer" includes matrices made from repeating units of two or more monomer repeats. As used herein, "polymer" also includes homopolymers and heteropolymers, a "homopolymer" being defined as a polymer consisting essentially of repeating units of identical monomers, and a "heteropolymer" being defined as a polymer consisting essentially of two or more monomers which are not identical, the monomers being repeated in a given order or randomly. A "mixed polymer" is defined herein as including two or more homopolymers or heteropolymers, or a combination of a homopolymer and a heteropolymer.

Exemplary monomer materials include acrylonitrile, acrylene, caprolactam, chloroprene, dichloroethene, ethylene, isoprene, propylene, tetrafluoroethene, vinyl chloride, vinylidene fluoride, acrylamide, amino acids, diisocyanate, divinylbenzene, ethylene glycol, formaldehyde, glycol, methyl methacrylate, styrene, sugars, terephtalic acid. Additional exemplary polymer materials include but are not limited to polysaccharides including cellulose, rayon, cellulose acetate, cellulose triacetate, chitin and agarose; protein/polypeptides including leather, silk and wool; synthetic gels including polyacrylamide, hydrogel (i.e., copolymer of poly(vinyl alcohol) and collagen); synthetic fibers including polyamides (nylon), polyesters, polyacrylonitrile (acrylic), polyurethane (spandex); and synthetic plastics including polycarbonate, phenol-formaldehyde resins, polysulfide, poly(vinyl butyryl), poly (vinyl chloride), poly(vinylidene chloride), poly(ethylene), and polystyrene.

The present invention does not utilize ion-exchange procedures, affinity binding, density gradients, phase separation, or physical trapping to separate the nucleic acids from other cellular or tissue components. Thus, removal of large amounts of salt, as is present in samples having been prepared by such methods, or further purification of nucleic acids, as is necessary for samples having been prepared using gradients, is not necessary. Moreover, the method of the invention is fast and the yield of recovery for large sizes of nucleic acids is superior to other methods of the prior art.

The invention features methods and devices for the efficient and quantitative recovery of relatively small amounts of nucleic acid from plural samples by binding to a matrix having the characteristics described herein.

The nucleic acid to be isolated can be present in any type of biological sample, and will generally be a sample of medical, veterinary, forensic, environmental, nutritional, scientific or industrial significance. Human and animal specimens and body fluids particularly can be assayed by the present method, providing that they contain cells, or particles, e.g., virions, from which nucleic acid can be prepared. Preferred sources include blood, sperm, any mammalian tissue, milk, urine, cerebrospinal fluid, sputum, fecal matter, and lung aspirates, all of which may have been collected as is or previously adsorbed onto a fluid collection device such as a swab; in addition, buccal cells, throat swabs, genital swabs and exudates, rectal swabs, and nasopharyngeal aspirates.

The invention allows for simultaneous recovery of exceedingly small amounts of nucleic acid from, e.g., hundreds of a type of sample in a quantitative manner. Typically 70–100%, and more likely at least 80%, 90% or most likely at least 95%, of the nucleic acid that is present in a biological sample may be recovered according to the invention, even when the sample contains such small amounts as less than 1 ng of nucleic acid. For example, as much as 0.3–0.4 $\mu$g of genomic DNA may be recovered from a 15 $\mu$l dried blood spot according to the invention. Because the invention allows for recovery of the isolated nucleic acid into a relatively small volume of liquid, e.g., smaller than 500 $\mu$l, 250 $\mu$l, 100 $\mu$l, and even as small as 5–10 $\mu$l, the invention avoids the risk of loss of the recovered nucleic acid encountered in concentrating a sample from a relatively large volume.

The nucleic acid may be isolated or concentrated according to the invention from an impure, partially pure, or a pure sample. The purity of the original sample is not critical to the inventive methods, as nucleic acid may be isolated from even grossly impure samples according to the invention. For example, nucleic acid may be removed from an impure sample of a biological fluid such as blood, saliva, or tissue. If a sample of higher purity is desired, the sample may be treated according to any conventional means known to those of skill in the art prior to undergoing isolation according to the invention, e.g., the sample may be processed so as to remove certain impurities such as insoluble materials from an impure sample prior to nucleic acid isolation.

Methods of the invention may be performed on a biological sample which has been deposited on any type of material, provided the material itself does not form cross-linkages to retain the nucleic acid irreversibly. Thus, the sample may be contained within a material such as paper, textile, e.g., a fragment of an article of clothing, agarose, or polyacrylamide. One example of a sample and sample matrix according to the invention is a drop of a body fluid, e.g., blood, which has been stored dry on a piece of Schleicher and Schuell #903 paper, the paper routinely used nationwide for the purpose of newborn screening.

For purposes of the following description of the invention, recovery of nucleic acid in the form of genomic DNA, plasmid DNA, or single-stranded DNA or RNA is described in detail herein. However, it is to be understood that the invention encompasses recovery of any form, whether fragmented, circular, single stranded (RNA and some bacteriophage and virus DNAs and RNAs) or chromosomal DNA.

The method of the invention is applied to isolation of nucleic acid from a biological sample, as follows.

Tissues or cells that contain nucleic acids are suspended in an extraction solution that contains a buffer system, a detergent, and a chelating agent. The buffer system can be any buffer, e.g., TrisHCl, sufficient to maintain pH values from approximately 5.0 to approximately 10. The detergent can be ionic or nonionic detergent, such as sodium dodecyl sulfate (SDS) or octylglucoside, at a concentration sufficient to lyse cells and denature proteins. A chelating agent, such as EDTA, captures free divalent ions ($Mg^{2+}$) so that nucleic acids are more soluble and protected from degradation by DNA-degrading enzymes that require $Mg^{2+}$.

A protease may also be added to the extraction mixture to digest proteins so that the nucleic acids can be easily released from the cells and so that the proteins are degraded to small peptides and become more soluble in solution. Any non-specific or specific protease may be used, for example, proteinase K, trypsin, chymotrypsin, or V8 protease.

Nucleic acid aggregates are next formed by precipitating the nucleic acid. Structurally, nucleic acid possesses a phosphodiester backbone that is negatively charged around neutral pH. Nucleic acid becomes insoluble (i.e., precipitated) in the presence of salts and agents that can reorganize its aqueous environment. Acetone, alcohols such as ethanol and isopropanol, and soluble organic polymers, such as polyethylene glycol (PEG) are examples of useful precipitants. Co-precipitants, such as glycogen, also may be used to facilitate the precipitation of nucleic acid present in only small quantities; for example, in the form of heteroaggregates. The presence of a co-precipitant is not required according to the invention, but serves to increase the efficiency of aggregate formation. In the presence of moderate concentrations of monovalent salt, the charges in nucleic acids are neutralized so that nucleic acid aggregates are formed and stabilized by Van der Waals forces. Divalent salts such as magnesium chloride or calcium chloride can also be used to precipitate nucleic acids.

As indicated above, the matrix may be any matrix that reversibly binds nucleic acid. In preferred embodiments described in detail herein, cellulose, agarose powder, and polyacrylamide are used as matrices. Where the matrix is fibrous, the fibers may be mechanically broken to 1 to 2 mm fibers. The matrix is washed to remove salts and other contaminants. The matrix can either be stored dry or in an aqueous solution at room temperature in a concentration convenient for use. The matrix may be used in a column format, for example, in a pipet tip, syringe, or larger column, or in suspension.

Once the matrix is prepared, the matrix is added to the suspension containing the nucleic acid aggregate, or the nucleic acid aggregate suspension is allowed to bind to the matrix in the column. Unbound materials, such as digested proteins, lipids, and other unwanted cellular components are then separated from the bound nucleic acid aggregates by retaining the nucleic acid/matrix complexes in a column or a filter. In one embodiment, when the matrix is in a column format, the bound, aggregated nucleic acids may be purified by washing the column with a buffer to wash away the undesirable materials. Once these materials are removed, the aggregated nucleic acid may be recovered by eluting them from the matrix material after dissolving the aggregates in water or low salt buffer. The recovered nucleic acid is substantially pure, concentrated, and suitable for immediate use in subsequent experiments.

The invention is better illustrated with respect to the following examples. These examples are meant to be illustrative of carrying out the invention, and not to be limiting with respect to the spirit and scope of the invention and the claims.

EXAMPLE 1

Isolation of DNA Using Cellulose Matrix

Materials and reagents used in this Example and in general are as follows:

TE: 10 mM TrisHCl, pH 8.0 and 1 mM EDTA.
Matrix solution: 50 mM TrisHCl, pH 8.0, 10 mM EDTA.
Washing solution: 6 parts of ethanol mixed with 4 parts of buffer containing 200 mM NaCl, 50 mM TrisHCl, pH 8.0, 5 mM EDTA.
Extraction buffer: 1% SDS, 50 mM TrisHCl pH 8.0, 10 mM EDTA. Dithiothreitol (25 mM DTT final concentrations, optional) and proteinase K (final concentration 50 µg/ml) are added before use.
Precipitant: isopropanol.
Salt solution: 5 M NaCl.
Co-precipitant: glycogen (5 µg/µl).
Elution buffer: 5 mM TrisHCl, pH 9, 0.5 mM EDTA.
TBE buffer: 45 mM Tris-Boric acid and 1 mM EDTA.

Filter paper consisting essentially of cellulose (0.25 g of Whatman 3 MM paper) is cut into <4 mm² pieces and suspended in about 10 ml of matrix solution, followed by vigorous vortexing until the paper becomes fibrous. The suspension is filtered through a membrane with 0.45 micron pores to remove liquid and the fibers are recovered from the filter. The wet fibers are then subjected to the procedure of cutting-vortexing-filtration twice so that all cellulose fibers are dissociated. The fibrous matrix thus formed is stored in either 50 ml matrix solution or 50 ml washing solution at room temperature (5 mg/ml). When stored in this manner, the fiber suspension is free to pass through a pipet with 2 mm opening. The volume that the 0.25 g matrix occupies after settling is equivalent to 10 ml–12.5 ml.

P-200 pipet tips are used as columns to hold matrix. A piece of KimWipe paper (5×5 to 6×6 mm²) or long cotton fibers are placed inside a tip in a position of about 10 mm from the small opening to create a filter or barrier to support the matrix. A P-1000 tip with 2–4 mm opening at the sharp end is attached to the top of the column as a funnel. The matrix suspension (0.5 ml–15 ml) is added to the funnel-column unit under vacuum to form a column bed. The height of the column bed is about 5–15 mm, depending on amounts of matrix used. Columns prepared as above are washed with either water or TE then equilibrated with washing solution before being used for nucleic acid isolation.

Test DNA samples include 9 µg of lambda DNA and 90 µg of glycogen diluted in elution buffer to total 450 µl (Sample A); and 31.5 µg of Salmon Testes DNA and 90 µg of glycogen diluted in elution buffer to total 450 µl (Sample B).

The procedure for purifying the DNAs is as follows:

1. 50 µl of Sample A (1 µg DNA) and 50 µl of Sample B (3.5 µg DNA) are reserved as controls. The 400 µl of each remaining sample is diluted to 4 ml with extraction buffer. NaCl concentration is adjusted to 200 mM.

2. 5 ml of isopropanol is mixed with each of the samples in extraction buffer. The solutions are incubated at room temperature for 30 min to precipitate the DNAs.

3. Aliquots of about 1.1 ml of each DNA suspension (1 µg or 3.5 µg DNA) are loaded onto pre-equilibrated columns containing 0, 2.5, 3.75, 5 mg matrix fibers, respectively. The columns may be connected to a vacuum manifold in this and subsequent steps.

4. Each column is washed twice with 1 ml of washing solution; vacuum may be applied to speed the washing. Finally, the column is dried by centrifugation (i.e., in a microcentrifuge) at 5 k rpm for 1 min.

5. 50 µl of elution buffer is added to each dried column bed and the rehydrated columns are allowed to stay at room temperature for 5 min.

6. Each rehydrated column is placed in a 1.5–ml tube and DNA in the column is recovered into the tube by centrifugation at 5 k rpm for 1 min. Approximately 50 μl is recovered.

7. 40 μl of each sample is diluted 1:1 with water and optical densities are determined at 260 nm and 280 nm for each diluted sample.

8. 10 μl of each control DNA and 10 μl of each recovered DNA are separated by electrophoresis in 0.8% agarose gel in TBE buffer containing 0.5 μg/ml of ethidium bromide.

The DNA recovery rates are correlated to the height of a column bed. As determined by UV absorption, DNAs are almost completely recovered by columns filled with 5 mg matrix (100% for lambda DNA and 98.9% for Salmon Testes DNA). About half of the DNA is recovered (54% for lambda DNA and 53% for Salmon Testes DNA) when columns are filled with 2.5 mg matrix. Little DNA is recovered from columns with Kim-Wipe filter only.

For a column prepared in a P-200 tip, 10–15 mm of column bed height is sufficient to get high yield recovery when less than 20 μg of nucleic acids are to be purified. DNA may be eluted from such a column in less than 50 μl water or buffer and ready for immediate use. Results from agarose gel electrophoresis show that the band patterns between DNAs recovered from columns and control DNAs are identical. Both large DNA (48.5 kb and larger) and small DNA (0.3 kb and smaller) are equally recovered from the columns. High yield recovery of both large and small DNA is one of the most distinguishing features of this method.

EXAMPLE 2

Isolating DNA from Dried Blood Spots on Filter Paper Using Cellulose Matrix

Solutions and reagents are the same as those used in Example 1 unless otherwise specified. In addition, 1 M $MgCl_2$ and chelating resin are used. Column matrix and columns are prepared as in Example 1 unless otherwise specified.

4 full circles (15 mm diameter) of dried blood spots are removed from S&S 903 filter papers. Two of them are immersed in 5 ml of extraction buffer (Sample 1) and the other two are placed in 5 ml of the same buffer plus 0.1 g chelating resin (Sample 2). The samples are incubated at 56° C. for about 2 hours to digest proteins by proteinase K.

A. Phenol-extraction and ethanol precipitation (control method):

1. 500 μl of Sample 1 (designated 1-0) and 500 μl of Sample 2 (designated 2-0) are extracted with 500 μl of phenol:chloroform twice.

2. Glycogen is added to 20 μg/ml and NaCl is added to 0.1M.

3. 1 ml ethanol is mixed with the extracted samples to precipitate nucleic acids at −20° C. for 2 hours.

4. Precipitated nucleic acids are collected by centrifugation for 15 min at 12 k rpm and finally dissolved in 50 μl of water.

B. Matrix method (method of the invention):

1. 4 aliquots of 500 μl (1-1 to 1-4) are retrieved from Sample 1, and the same for Sample 2 (2-1 to 2-4). NaCl was added to 0.1M in each.

2. The samples are mixed with co-precipitants: glycogen (10 μg in 1-1, 1-2, 2-1, 2-2) and $Mg^{2+}$ (final concentration 20 mM in 1-1, 1-3, 2-1 and 2-3).

3. Isopropanol (650 μl) is mixed with each sample and the mixtures are incubated at room temperature for 20 min to precipitate nucleic acids.

4. Precipitated nucleic acids are loaded onto pore-equilibrated columns (5 mg matrix each) connected to a vacuum manifold unit.

5. The columns are washed twice with 1 ml washing solution under vacuum and dried by centrifugation at 5 k rpm for 1 min.

6. 50 μl of elution buffer is added to each dried column bed to dissolve nucleic acids at room temperature for 5 min. The nucleic acids in a column are recovered into a 1.5 ml tube by centrifuging the column-containing tubes at 7 k rpm for 2 min.

5 μl of each control sample (1-0 and 2-0) and the samples purified by columns are separated in 1% agarose gel containing 0.5 μg/ml of ethidium bromide by a standard method.

The same amount of nucleic acid (mainly DNA) is recovered by the column method as by the control method, based on gel electrophoresis analysis. Samples treated with chelating resins contained DNAs of relatively large molecular weights.

DNA isolated from filter paper by the nucleic acid isolation method described herein is consistently found to be compatible with DNA modifying enzymes. The DNA thus-isolated is also digestible by restriction enzymes such as ScrF1, and can be used for polymerase chain reaction (PCR).

Thus, high yield isolation of nucleic acid from small quantities of clinical samples may easily be achieved using the method of the invention. Because high speed centrifugation (>10,000 rpm) is not required, the method can be easily automated. The total isolation time for solubilized nucleic acids may be shorter than 30 min.

EXAMPLE 3

Isolation of Plasmid DNA Using Cellulose Matrix

Reagents, matrix and columns are the same as in Example 1 unless otherwise specified. In addition, a plasmid isolation kit (Wizard Kit) from Promega was used for comparison. LB media used in this example contained 1% tryptone, 0.5% yeast extract and 1% NaCl in water.

Source of double-stranded plasmid DNA: E. coli cells harboring pbluescript plasmid (Stratagene) are grown overnight in LB media containing ampicillin (100 μg/ml).

Source of single-stranded plasmid DNA: E. coli cells harboring pbluescript plasmid (Stratagene) are infected by M13K07 helper phages (NEB) to generate single-stranded plasmid DNA. The cells are grown overnight at 37° C. in LB media containing ampicillin (100 μg/ml) and kanamycin (70 μg/ml).

To purify double-stranded plasmid DNA, the following steps are performed:

1. An overnight culture is split into 6 aliquots of 1-ml samples (A-1 to A-6).

2. Crude plasmid DNA is obtained by alkaline lysis method with reagents in the Wizard plasmid isolation kit, following instruction from the manufacturer.

3. DNAs in samples A-1 to A-3 are further purified with silica powder provided in the same Wizard kit. Each DNA sample is finally recovered in 50 μl of water.

4. Other crude DNA samples (A-4 to A-6) are mixed with 750 μl of isopropanol and incubated for 20 min at room temperature.

5. Precipitated DNAs are loaded onto pre-equilibrated columns, each containing 5 mg matrix and prepared as described in Example 1.

6. Column Washing and DNA recovering are the same as described in Example 1. DNA in each column is eluted in 50 µl of elution buffer.

To purify single stranded plasmid DNA, the following steps are performed:

1. 8 clear supernatants of 1 ml (B-1 to B-8) are recovered from a helper phage-infected culture after removal of cells by centrifugation.

2. 250 µl of PEG solution (20% polyethylene glycol-8000 plus 2.5M NaCl) is mixed with each of the 8 samples. The solutions are kept at room temperature for 15 min.

3. Precipitated phage particles are harvested by centrifugation at 10 k rpm for 5 min at room temperature.

4. After complete removal of the liquid, 500 µl of extraction buffer is added to each pellet and incubated at 56° C. for 40 min to release DNA. NaCl is then added to 0.2M.

5. 4 samples (B-1 to B-4) are subjected to phenol:chloroform extraction twice followed by ethanol precipitation as described in Example 2. The DNA pellets are dissolved in 50 µl of TE buffer.

6. The other 4 samples (B-5 to B-8) are mixed with 10 µg glycogen and 625 µl of isopropanol, followed by purification with columns as described in Example 1. Each DNA sample is dissolved in 50 µl of elution buffer.

5 µl of each purified DNA is separated in a 1% agarose gel containing 0.5 µg/ml ethidium bromide for analysis.

The results demonstrate that similar amounts of double-stranded plasmid DNAs are isolated with cellulose matrix as with a silica matrix. Single-stranded plasmid DNAs are also isolated, although the amount of DNA isolated by the cellulose matrix method is slightly less than that isolated after phenol extraction and ethanol precipitation. DNAs isolated by the cellulose matrix method are sequenced as efficiently as DNAs isolated by phenol extraction and ethanol precipitation method. Plasmid isolation by this method of the invention eliminates the use of chaotropic agents and minimizes the use of high speed centrifugation.

EXAMPLE 4

RNA Isolation Using Cellulose Matrix

Solutions and reagents are the same as in Example 1 unless otherwise specified.

RNA may be isolated by the following steps:

1. 1 g of fresh and soft plant leaves is ground in 5 ml of TRIzol (Life Technologies) to release nucleic acid.

2. The homogenate is separated by centrifugation and two clear supernatants of 1 ml each are collected. Each of the supernatants is mixed with 600 µl of chloroform. 750 µl of the aqueous solution is recovered from each tube after centrifugation and is placed in a clean tube.

3. 750 µl of isopropanol is mixed with each solution and the resulting solutions are kept at room temperature for 20 min to precipitate the nucleic acids.

4. Nucleic acid in one tube (A) is harvested by centrifugation (12,000 rpm) for 15 min at room temperature. The pellet is dissolved in 75 µl of water after removal of liquid and drying the pellet. 25 µl of the sample is diluted 1:1 with 25 µl of water and the resulting solution is designated as A1 and the remaining 50 µl A2.

5. Nucleic acid precipitated by isopropanol in the other tube (B) is divided to 500 µl (B1) and 1000 µl (B2). Nucleic acid in the two solutions are subjected to column purification as described in Example 1. The nucleic acid from each sample is dissolved in 50 µl water.

6. 5 µl of each sample (A1, A2, B1, B2) may be subjected to agarose gel electrophoresis (1.2%, 0.5 µg/ml ethidium bromide).

7. 400 µl water is added to each sample and the resulting solutions are examined by a UV spectrophotometer.

RNAs of small (tRNA) and large (rRNA) sizes are isolated with the cellulose matrix, and DNA of very high molecular weights is also present. The band patterns of the RNAs obtained by the two methods are identical. Sample A2 contained the largest amount (114 µg) of nucleic acids (mainly RNA) and sample A1 contains approximately half (62 µg) as much as A2. Sample B1 has nearly the same amount (53 µg) of nucleic acids as A1. Sample B2 recovers approximately 81 µg.

In this example, A1 and A2 are prepared by the complete TRIzole method, and B1 and B2 by a modified method in which the cellulose column procedure is used to replace high speed centrifugation. Thus, the quality of the RNAs are expected to be as good as that isolated by the complete TRIzole method. The column procedure may be more reliable for isolating small quantities of nucleic acids (<20 µg) because pellet formation is not required.

EXAMPLE 5

DNA Isolation Using Agarose Matrix

Solutions and reagents were the same as in Example 1 unless other specified. Dry agarose powder (FMC, Type LE) is suspended in water at room temperature at a concentration of approximately 5 mg/ml. Large particles are used to pack columns as described in Example 1 in order to obtain a reasonable flow rate. The column bed length is about 15 mm. Columns are washed with water and matrix solution before they are used for DNA isolation.

DNA sample preparation (1.75 µg of Salmon Testes DNA for each sample) and isolation procedures are the same as described in Example 1. Isolated DNAs are analyzed by agarose gel and optical density measurement as described in Example 1. About 92% of DNA can be recovered by the agarose matrix, compared to those recovered by ethanol precipitation when the same amounts of DNA are used.

EXAMPLE 6

DNA Isolation Using Synthetic Fiber Matrix

Solutions and reagents are the same as in Example 1 unless otherwise specified. Synthetic cotton from a cosmetic puffball (purchased from a local department store) is cut to short fragments (1–2 mm). Columns are made as described in Example 1, using the synthetic fibers as matrix. The column bed is about 12 mm long.

Sample preparation, DNA isolation and analysis are the same as described in Example 5. About 50% of DNA is recovered with this matrix, compared to those recovered by ethanol precipitation when the same amounts of DNA were used. This relative low yield of recovery is expected due to the lower hydrophobicity of this matrix compared to a cellulose matrix.

EXAMPLE 7

DNA Isolation Using Polyacrylamide Matrix

Solutions and reagents are the same as in Example 1 unless otherwise specified. 7.5 ml of 30% acrylamide/bisacrylamide solution and 7.5 ml of water were mixed. A 15% polyacrylamide gel was formed and is broken into fine particles (0.5–1.5 mm) mechanically. The suspension is washed with water extensively until soluble materials and unpolymerized acrylamide are removed.

Columns are prepared as described in Example 1 except that the polyacrylamide particles are used as a matrix. The column bed is about 15 mm high when hydrated. Sample preparation and subsequent purification procedures are essentially the same as described in Example 2. DNA is recovered in basically the same yield by the polyacrylamide matrix as by cellulose matrix.

A summary of recovery of nucleic acids, relative to a 100% recovery of nucleic acid using the phenol or silica isolation methods described hereinabove, is provided in Table I.

In Table I, the following key is used. Phenol refers to phenol/chloroform extraction followed by ethanol precipitation; Silica refers to a silica glass powder matrix for DNA purification; CF refers to a cellulose fiber matrix for DNA purification; Agarose refers to agarose powder matrix for DNA purification; Synthetic refers to a synthetic cotton fiber matrix for DNA purification; PAG refers to a polyacrylamide gel suspension matrix for DNA purification.

In Table 1, the DNA referred to is as follows. Lambda: lambda DNA; Salmon: salmon testes DNA; DBS: dried blood spot DNA; DSP: double stranded plasmid DNA; SSP: single stranded plasmid DNA; Plant: plant RNA. In addition, each number refers to percentage of recovery, control is 100%; NA refers to not applicable, or not available;+refers to the same or nearly the same as controls.

TABLE I

| Method | Form or source of nucleic acids | | | | | |
|---|---|---|---|---|---|---|
| | Lambda | Salmon | DBS | DSP | SSP | Plant |
| Phenol | 100 | 100 | 100 | NA | 100 | 100 |
| Silica | NA | NA | NA | 100 | NA | NA |
| CF | 100 | 99 | + | + | 70–80 | + |
| Agarose | NA | 92 | NA | NA | NA | NA |
| Synthetic | NA | 50 | NA | NA | NA | NA |
| PAG | NA | NA | + | NA | NA | NA |

Figure 1:
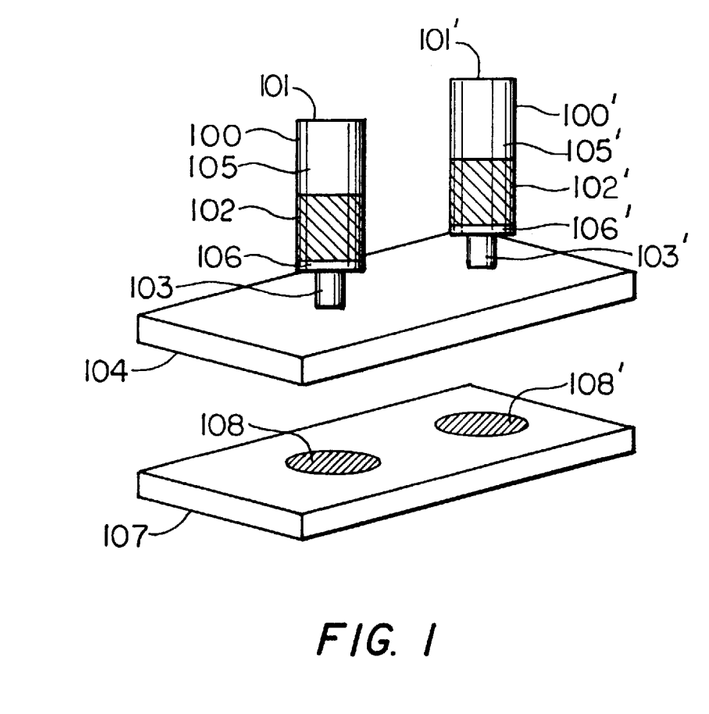
FIG. 1 is a diagram of an embodiment of the invention employing a sample collection tray.

As illustrated in FIG. 1, an apparatus of the invention will include plural housings 100, 100' and a planar surface support 104 for convenient simultaneous handling of the plural housings. Each housing 100, 100' possesses an inlet 101, 101' and an outlet 103, 103', and defines a flowpath 105, 105' for flow of liquid therebetween. Housings 100, 100' contain matrix 102, 102', as defined and described herein. The plural housings and surface support 104 may be an integral unit, or the housings may be separate from and adapted to fit into the support 104. The housings may also include barrier means 106, 106' near the outlet end 103, 103', which barrier means serves to prevent matrix from exiting the outlet of the housing. The support 104 may be a plate or tray containing holes into which the housings fit, or it may be a simple wire or plastic rack. The apparatus may optionally include a collection surface 106 which is positioned beneath the support surface 104. The collection surface is also a planar surface which includes sample collection sites 108, 108'. Sites 108, 108' may be simple indentations on the surface of a plastic plate or they may be cups or tubes, e.g., microfuge tubes, which fit into the plate. Collections sites 108, 108' may be water insoluble, such as plastic, for collection of liquid flowthrough from the housing, or they may be absorbent pieces of filter paper for absorbing flowthrough. Sites 108, 108' are for collecting liquid that flows through the housing, whether it be matrix washings of unwanted material or eluted nucleic acid. During operation, the apparatus may include two collection surfaces of the format of surface 106, a first collection surface 106 for collection of unwanted materials which flow through the housings, and the second collection surface 106 for collection of eluted nucleic acid. The collection surface 106 may lie beneath surface 104; however, optimally, surface 106 will fit snugly within the edges of surface 104. In the embodiment of the invention shown in FIG. 1, flow through may be collected using gravity flow or by centrifugation of the entire apparatus, or by pressure applied from top of the housing.

Figure 2:
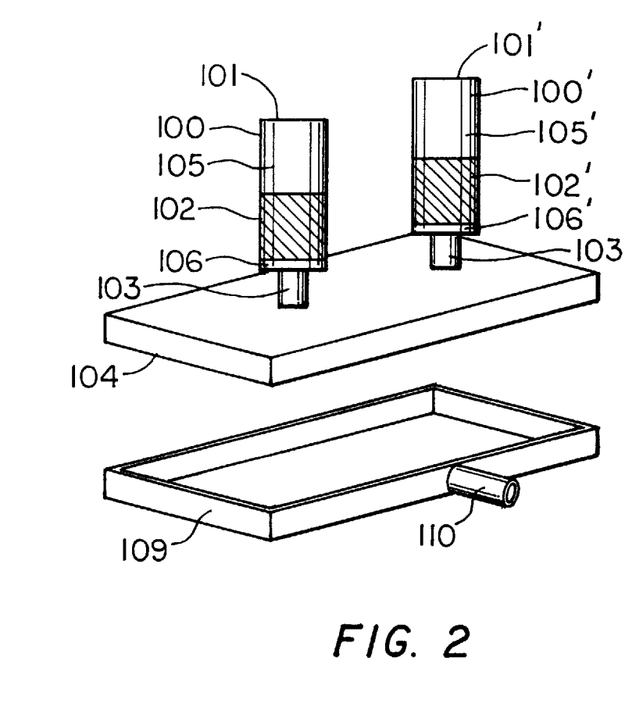
FIG. 2 is a diagram of another embodiment of the invention adapted for connection to a vacuum source.

Alternatively, as shown in FIG. 2, the apparatus may include dish 109, which may include means for connecting 110 the apparatus to a vacuum source to assist in washing the matrix. A vacuum source may be connected to the vacuum connecting means 110 and a vacuum applied to suck excess solutions from the column. Vacuum connecting means 110 may include a connector such as a compression fitting, ferrule, coupling, or other structure known in the art capable of accepting and holding a vacuum. Although gravity flow may be used to pull liquid through the housing, use of a vacuum unit expedites the method of the invention.

The apparatus shown in FIG. 2 also may be combined with the apparatus shown in FIG. 1. That is, surface support 104, containing plural housings 100, 100', and collection tray 106 may be used along with dish 109 such that the collection tray 106 fits snugly within dish 109. When vacuum is applied to the apparatus via connecting means 110, the vacuum pulls liquid through the housing, matrix, outlet, and onto the collection sites 108, 108'.

In operation, plural biological samples in liquid form are applied to the inlet 101 of the plural housings, whereupon each sample flows along flow path 105 into and through the matrix 102. Contact between nucleic acid in the sample and the matrix results in binding of nucleic acid to the matrix. Nucleic acid is thus retained, while unwanted components of the biological sample flow through the matrix and screen 106, and exit via outlet 103. The matrix may be washed prior to, during, or after nucleic acid binding, if desired.

After binding, which may take no longer than a few minutes, or the time interval in which the liquid sample flows through the matrix, bound nucleic acid is eluted from plural matrices simultaneously by dispensing elution buffer into the plural housings and fitting the support plate 104 over the sample collection tray 106. Centriguation and gravity may be used to pull the elution buffer through the matrix (FIG. 1). Alternatively, a vacuum source may be connected to dish 109 and support plate 104 may be placed over dish 109 to expedite flowthrough (FIG. 2). If desired, support plate 104, collection plate 106 and dish 109 may be sandwiched together for simultaneous isolation of plural nucleic acid samples. If desired, the unit can be modified so that liquid can flow through the housing under pressure applied to 101 or 101', and samples are collected via 108, 108'.

OTHER EMBODIMENTS

Other embodiments will be evident to those of skill in the art. Although the invention has been shown and described with respect to an illustrative embodiment thereof, it should be appreciated that the foregoing and various other changes, omissions, and additions in the form and detail thereof may be made without departing from the spirit and scope of the invention as delineated in the claims.

I claim:

1. A method of isolating nucleic acid in a substantially purified form, said method comprising the steps of:
   a) contacting a biological sample containing nucleic acid with a matrix under conditions which permit said nucleic acid in said sample to bind to said matrix, said matrix consisting essentially of agarose particles in liquid suspension so as to bind said nucleic acid to said matrix, wherein said conditions also permit said nucleic acid in said sample to precipitate; and
   b) eluting said nucleic acid from said matrix.

2. The method of claim 1, further comprising the step of contacting said biological sample with a proteolytic enzyme under conditions sufficient to subject said sample to proteolysis.

3. A method for isolating nucleic acids in a substantially purified form, said method comprising the steps of:
   a) providing a matrix consisting essentially of agarose particles in liquid suspension;
   b) contacting a biological sample comprising nucleic acids with the agarose matrix under conditions which permit said nucleic acids to bind to said matrix, wherein said conditions also permit said nucleic acids in said sample to precipitate; and
   b) eluting said nucleic acids from said matrix.

4. The method of claim 1, further comprising tie step, prior to step a) of precipitating said nucleic acid in said biological sample.

5. The method of claim 1, wherein said solution comprises a precipitating ingredient selected from the group consisting of organic solvents, soluble organic polymers and salts.

6. The method of claim 5, wherein the organic solvent may be any one of isopropanol, ethanol, and acetone.

7. The method of claim 5, wherein said organic polymer consists essentially of polyethylene glycol.

8. The method of claim 5, wherein said salt is one of NaCl and LiCl.

9. A method of isolating nucleic acids in a substantially purified form, said method comprising the steps of:
   a) contacting a biological sample containing nucleic acids with a matrix under conditions which permit said nucleic acids to bind to said matrix, said matrix consisting essentially of cellulose fiber in liquid suspension, wherein said conditions also permit said nucleic acids in said sample to precipitate; and
   b) eluting said nucleic acids from said matrix.

10. A method of isolating nucleic acids in a substantially purified form, said method comprising the steps of
    a) contacting a biological sample containing nucleic acids with a matrix under conditions which permit said nucleic acids to bind to said matrix, said matrix consisting essentially of polyacrylamide gel particles in liquid suspension, wherein said conditions also permit said nucleic acids in said sample to precipitate; and
    b) eluting said nucleic acids from said matrix.

11. A method for isolating nucleic acids in a substantially purified form, said method comprising the steps of:
    a) providing a matrix consisting, essentially of dissociated cellulose fibers in liquid suspension;
    b) contacting a biological sample comprising nucleic acids with the cellulose matrix under conditions which permit said nucleic acids to bind to said matrix, wherein said conditions also permit said nucleic acids in said sample to precipitate; and
    c) eluting said nucleic acids from said matrix.

12. A method for isolating nucleic acids in a substantially purified form, said method comprising he steps of:
    a) providing a matrix consisting essentially of polyacrylamide gel particles in liquid suspension;
    b) contacting a biological sample comprising nucleic acids with the polyacrylamide gel matrix under conditions which permit said nucleic acids to bind to said matrix, wherein said conditions also permit said nucleic acids in said sample to precipitate; and
    c) eluting said nucleic acids from said matrix.

13. The method of any one of claim 9 or 11, wherein said cellulose fibers are prepared by cutting cellulose.

14. The method of claim 9 or 11, wherein said cellulose fibers are about 5–500 microns in length.

15. The method of claim 9 or 11, wherein said cellulose fibers are about 0.1–10 millimeters in length.

16. The method of any one of claims 1 or 9–12 wherein said eluting step b) comprises recovering at least 70% of the nucleic acid contained in said biological sample of said step a).

17. The method of any one of claims 1 or 9–12 wherein said eluting step b) comprises recovering at least about 90% of the nucleic acid contained in said biological sample of said step a).

18. The method of any one of claims 1 or 9–12 wherein said nucleic acid of said eluting step b) is at least about 90% pure with respect to salts and anticoagulants inhibitory to a polymerase chain reaction.

19. The method of any one of claims 1 or 9–12 wherein said eluting step b) comprises eluting said nucleic acid wherein the quantities of large and small DNAs are proportional to the quantities of large and small DNAs in the nucleic acid contained in the biological sample of said step a).

20. The method of any one of claims 9–12, further comprising the step, prior to step a) of precipitating said nucleic acid in said biological sample.

* * * * *